United States Patent [19]
Allen

[11] Patent Number: 6,149,932
[45] Date of Patent: *Nov. 21, 2000

[54] DIETARY SUPPLEMENT FOR PREVENTING OR REDUCING SHEDDING OF HAIR

[75] Inventor: Barabra A. Allen, Farmington, Conn.

[73] Assignee: Stabar Enterprises, Inc., Farmington, Conn.

[ * ] Notice: This patent is subject to a terminal disclaimer.

[21] Appl. No.: 09/183,933

[22] Filed: Oct. 30, 1998

Related U.S. Application Data

[63] Continuation-in-part of application No. 09/047,092, Mar. 24, 1998, Pat. No. 5,965,153.

[51] Int. Cl.$^7$ ..................................................... A23K 1/165
[52] U.S. Cl. ............................................ 424/439; 424/401
[58] Field of Search ...................................... 424/442, 401, 424/489, 78.02, 78.06, 72, 439

*Primary Examiner*—Thurman K. Page
*Assistant Examiner*—William E. Benston, Jr.
*Attorney, Agent, or Firm*—Cooper & Dunham LLP

[57] ABSTRACT

A dietary supplement for humans and hair-bearing pets such as dogs and cats, comprising safflower oil, sunflower oil, olive oil, soya oil, cod liver oil, lecithin, natural flavors, herbs, garlic, and zinc. When fed to a dog or cat daily in a proper dosage, the supplement reduces or eliminates non-seasonal shedding and promotes healthy skin and a glossy coat, silky coat, without affecting the dog's or cat's natural shedding cycle and without causing any harmful effects. The composition also may be administered topically to a human to reduce hair loss.

25 Claims, No Drawings

DIETARY SUPPLEMENT FOR PREVENTING OR REDUCING SHEDDING OF HAIR

This application is a continuation-in-part of U.S. Ser. No. 09/047,092, filed Mar. 24, 1998, now U.S. Pat. No. 5,965,153 the contents of which are hereby incorporated by reference into this application.

BACKGROUND OF THE INVENTION

The present invention relates generally to compositions and methods for preventing or reducing shedding of hair by hair-bearing mammals. More specifically, the present invention relates to a dietary supplement and methods for using the dietary supplement for humans, dogs, cats and other mammals. The compositions and methods described herein can be used to prevent pets from shedding out of season and to promote healthy skin and silky, glossy coats.

There are over 54 million domesticated dogs and over 63 million domesticated cats in the United States. The owners of these pets and other animals have had to cope with the problems associated with keeping the animals indoors and coming into frequent contact with the animals. Additionally, these pet owners deeply care for their pets and want to keep them as healthy and as beautiful as possible.

One of the problems pet owners often encounter is excessive amounts of pet hair clinging to clothes and fabrics and covering surfaces, including floors, carpets, and furniture. This is a result of shedding, the process by which many animals routinely lose their hair. New hair grows to replace that which is lost, so that the animals maintain a full coat.

Shedding is a normal process for certain animals and breeds, and should take place in those animals every spring. However, many individual animals shed throughout the year, not just during their natural shedding cycle. It is this unwanted, non-seasonal shedding that creates the year-round covering of pet hair found in the homes and on the clothes of pet owners.

Pet owners also are interested in keeping their pets healthy, and one aspect of that is healthy skin. Animals may be subject to myriad problems and diseases of the skin. Additionally, most pet owners want their pets to have a coat that is pleasing to the eye and to the touch. This is especially true for owners of show dogs, but is equally important to owners of household pets. It is desirable that pets have coats that look and feel healthy, glossy, and silky.

The present invention also relates to compositions and methods of preventing or reducing shedding of hair by humans. Currently several products are available on the market that are directed to treating hair loss. However, many of these products are known to be unsatisfactory for a variety of reasons. For example, some of the products are of synthetic origin and are known to produce unwanted systemic and local side-effects. In contrast, the present invention relates to compositions that are comprised of all natural ingredients. Moreover, the present compositions and methods are directed to preventing hair loss rather than aiding hair regeneration after the loss has already occurred.

In view of the above mentioned problems and considerations, the present invention contemplates a liquid composition that acts also as a dietary supplement to be taken daily which prevents or reduces hair shedding. Further, the compositions and methods of the present invention promote healthy skin and a silky, glossy coat in pets. Prior products on the market have not fully achieved the objective of preventing or reducing hair shedding in pets and humans. As described below, the present composition solves the problems and is safe and all-natural, does not interfere with the natural shedding cycle in case of pets and is highly palatable.

OBJECTS AND SUMMARY OF THE INVENTION

In view of the aforementioned considerations, it is an object of the present invention to provide a liquid composition that reduces or eliminates shedding of hair in mammals.

As used throughout this application, the term "mammal" or its grammatical equivalents means humans and domesticated hair-bearing pet animals such as dogs and cats.

It is another object of the present invention to provide a composition that, when ingested as a dietary supplement, fosters healthier skin in dogs and cats, including reduction of fungus infections and seasonal dry skin.

It is another object of the present invention to provide a liquid composition that fosters healthy, glossy, silky coats in dogs and cats.

It is yet another object of the present invention to provide a supplement for dogs and cats that reduces or eliminates non-seasonal shedding but does not interfere with their natural shedding cycles.

It is yet another object of the present invention to provide a dietary supplement for humans that reduces or eliminates shedding of hair.

It is another object of the present invention to provide a supplement for dogs and cats that is comprised entirely of natural products and is not harmful when ingested.

It is another object of the present invention to provide a dietary supplement for humans that is comprised entirely of natural products and is not harmful when ingested.

It is still another object of the present invention to provide a liquid dietary supplement that is highly palatable to dogs and cats when mixed with their normal daily food supply.

It is still another object of the present invention to provide a liquid dietary supplement that is highly palatable to humans.

It is another object of the present invention to provide a composition containing useful fish oils.

A further object of this invention is to provide a composition which can be administered as a dietary supplement.

The present invention contemplates a liquid composition comprising safflower oil, sunflower oil, olive oil, soya oil, cod liver oil, lecithin, natural flavors, herbs, garlic and zinc (and additional fish oils for cats). At least 3% of the composition is crude protein, at least 86% is crude fat, no more than 1% is crude fiber, and no more than 1% is moisture. When the proper dosage is administered to humans or mixed into a dog's or cat's food, once daily, as a dietary supplement, it has the effects of reducing or eliminating shedding of hair by the humans as well as reducing or eliminating non-seasonal shedding by the animal while fostering healthy skin and a glossy, silky coat on the animal.

DETAILED DESCRIPTION OF THE INVENTION

The present invention provides a liquid composition comprising: safflower oil, sunflower oil, olive oil, soya oil, cod liver oil, lecithin, natural flavors, herbs, garlic, and zinc. The relative percentages of these substances in the composition are in the order listed. The resulting composition contains at least 3% crude protein, at least 86% crude fat, no more than 1% crude fiber, and no more than 1% moisture.

The olive, soya and cod liver oils are an important source of vitamins A, B complex and E, and of linolenic and linoleic acids. Additional vitamins and anti-oxidants may be added to the composition where desirable.

Although the exact mechanism of operation of the composition is not known to the applicant, there appears to be a synergistic relationship between the oils and fatty acids which results in the significant achievements of the invention.

The composition preferably is mixed into a mammal's food once daily as a dietary supplement. In the case of a dog, the dosage depends on the dog's size. Generally, a dog weighing up to 20 pounds should be given one tablespoon daily, a dog weighing between 20 and 45 pounds should be given two tablespoons daily, a dog weighing between 45 and 75 pounds should be given three tablespoons daily, and a dog weighing over 75 pounds should be given four tablespoons daily. The supplement has a taste that dogs enjoy, or, at the very least, do not resist, and is therefore easy to administer.

If the supplement is properly taken, reduction or elimination of non-seasonal shedding by the dog occurs. Seasonal shedding is the loss of hair during an animal's naturally occurring shedding cycle. For many dogs, this occurs every spring. The present composition is designed to reduce or eliminate shedding during the rest of the year, at all times outside the dog's natural shedding cycle, and there are no known harmful effects of taking the supplement.

When properly taken, the supplement fosters healthy skin which includes the reduction or elimination of occurrences of fungus infections and seasonal dry skin. Further, the supplement creates a healthy looking and feeling coat. The dog's coat should be more glossy and silky as a result of taking a daily dose of the supplement.

The dosage for humans can vary depending on characteristics such as the age and body weight of the person. However, since the ingredients are all of natural origin, the dosage can be safely determined on a trial and error basis by the person or can be reasonably approximated from the data on dogs. For example, upto twelve tablespoons daily may be appropriate for an adult male.

In another preferred embodiment of the present invention, fish oils are added to the composition set forth above. This alternative formulation is specifically useful as a dietary supplement for cats. The positive results set forth above occur in a cat that ingests a proper dosage of the supplement daily, and there are no harmful effects as a result of taking the supplement. The dosage for cats can be determined by standard methods known in the art such as weight and age of the animal.

Although the compositions of the invention preferably are administered orally, the compositions may also be topically administered by rubbing into the coat and skin of the animal or into the scalp of a human.

Preferably, the crude fat of the composition provided by this invention comprises Omega-3 fatty acids not less than 5% by weight of the total fat and Omega-6 fatty acids not less than 35% by weight of the total fat.

The crude fat of the composition comprises fatty acids of which not less than 16% by weight are saturated fatty acids of the following formula:

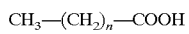

wherein n is an integer from 4 to 24.

In a preferred formulation, not less than 90% by weight of the total saturated fatty acids of the composition are comprised of the saturated fatty acids of the above formula wherein n is from 16 to 24. No more than 10% by weight of the total saturated fatty acids of the composition are comprised of the saturated fatty acids of the above formula when n is from 19 to 24. The fatty acids of the above formula when n is 16 together with the fatty acids of the formula when n is 18 comprise not less than 80% by weight of the total saturated fatty acids of the composition. Not less than 65% by weight of the saturated fatty acids of the composition are comprised of the fatty acids represented by the above formula when n is 16. Palmitic acid represents not less than 65% by weight of the saturated fatty acids of the composition.

Not less than 15% by weight of the fatty acids of the composition are comprised of the fatty acids represented by the formula when n is 18. In particular, stearic acid represents not less than 15% by weight of the total saturated fatty acids of the composition.

The composition presented in this invention has crude fat that further comprises fatty acids of which not less than 20% by weight are monounsaturated fatty acids represented by the formula:

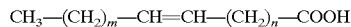

wherein each of m and n are independently the same as or different from each other and are each an integer from 1 to 19 provided that the sum of m and n is not less than 8 and does not exceed 20. Not less than 95% by weight of the monounsaturated fatty acids of the composition are comprised of the fatty acids represented by the above formula when the sum of m and n is from 12 to 20. The fatty acids of the above formula when m is 7 and n is 7, comprise not less than 90% by weight of the monounsaturated fatty acids of the composition. The fatty acids of the composition are present in cis configuration. Oleic acid represents not less than 90% of the total monounsaturated fatty acids of the composition. Preferably, the oleic acid of the composition is present in cis configuration.

The composition of this invention further provides crude fat which further comprises fatty acids of which not less than 50% by weight are polyunsaturated fatty acids represented by the formula:

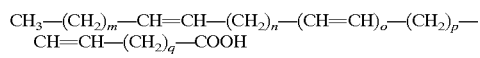

wherein each of m, n and q, are independently the same as or different from each other and each is an integer from one to seven; p is an integer from zero to seven; and o is either a zero or one, provided that the sum of m, n, o, p and q is not less than 9 and does not exceed 16; and provided that when o is zero then p is also zero.

In a preferred formulation, not less than 80% by weight of the polyunsaturated fatty acids of the composition are comprised of fatty acids of the above formula wherein m is 4, n is 1, o is zero, p is zero and q is 7. The polyunsaturated fatty acids are present in the cis, cis configuration. Linoleic acid represents not less than 80% by weight of the polyunsaturated fatty acids of the composition. Preferably, the linoleic acid is present in the cis, cis configuration.

In another embodiment, not less than 10% of the polyunsaturated fatty acids of the composition are comprised of the fatty acids represented by the formula when m is 1, n is 1, o is 1, p is 1, and q is 7. The polyunsaturated fatty acids are present in the cis, cis, cis configuration. In particular, linolenic acid represents not less than 10% of the polyunsaturated fatty acids of the composition and the linolenic acid is present in the cis, cis, cis configuration.

The embodiments described above are illustrative examples of the present invention and the present invention is not limited to these particular embodiments. Various changes and modifications may be made by one skilled in the art without departing from the scope or spirit of the invention as disclosed and claimed herein.

What is claimed is:

1. A composition for reducing or eliminating shedding of hair by a hair-bearing mammal comprising in combination safflower oil, sunflower oil, olive oil; soya oil; cod liver oil; lecithin; natural flavors; herbs; garlic and zinc; wherein not less than 86% of the composition is crude fat; wherein the crude fat further comprises Omega-3 fatty acids in not less than 5% by weight of the crude fat and Omega-6 fatty acids in not less than 35% by weight of the crude fat.

2. The composition according to claim 1, wherein the crude fat further comprises fatty acids of which not less than 16% by weight are saturated fatty acids of the following formula:

$$CH_3-(CH_2)_n-COOH$$

wherein n is an integer from 4 to 24.

3. The composition according to claim 2, wherein not less than 90% by weight of the saturated fatty acids are comprised of fatty acids of the formula wherein n is from 16 to 24.

4. The composition according to claim 3, wherein no greater than 10% by weight of the saturated fatty acids of the composition are comprised of saturated fatty acids of the formula when n is from 19 to 24.

5. The composition according to claim 3, wherein not less than 80% by weight of the saturated fatty acids of the composition are comprised of the fatty acids of the formula when n is 16 and 18.

6. The composition according to claim 3, wherein not less than 65% by weight of the total saturated fatty acids of the composition are comprised of the fatty acids represented by the formula when n is 16.

7. The composition according to claim 3, wherein palmitic acid represents not less than 65% by weight of the saturated fatty acids of the composition.

8. The composition according to claim 3, wherein not less than 15% by weight of the fatty acids of the composition are comprised of the fatty acids represented by the formula when n is 18.

9. The composition according to claim 3, which comprises stearic acid of not less than 15% by weight of the total saturated fatty acids.

10. The composition according to claim 1, wherein the crude fat further comprises fatty acids of which not less than 20% by weight are monounsaturated fatty acids represented by the formula:

$$CH_3-(CH_2)_m-(CH=CH)(CH_2)_n-COOH$$

wherein each of m and n are independently the same as or different from each other and are each an integer from 1 to 19 provided that the sum of m and n is not less than 8 and does not exceed 20.

11. The composition of claim 10 wherein not less than 95% by weight of the monounsaturated fatty acids of the composition are comprised of the fatty acids represented by the formula when the sum of m and n is from 12 to 20.

12. The composition of claim 10, wherein not less than 90% by weight of the monounsaturated fatty acids of the composition are comprised of the fatty acid of the formula when m is 7, and n is 7.

13. The composition of claim 10, wherein oleic acid represents not less than 90% of the monounsaturated fatty acids of the composition.

14. The composition of claim 12, wherein the fatty acid is present in cis configuration.

15. The composition of claim 13, wherein the oleic acid is present in cis configuration.

16. The composition according to claim 1, wherein the crude fat further compromises fatty acids of which not less than 50% by weight are polyunsaturated fatty acids represented by the formula:

$$CH_3-(CH_2)_m-CH=CH-(CH_2)_n-(CH=CH)_o-(CH_2)_p-CH=CH-(CH_2)_q-COOH$$

wherein each of m, n and q, are independently the same as or different from each other and each is an integer from one to seven; p is an integer from zero to seven; and o is either a zero or one, provided that the sum of m, n, o, p and q is not less than 9 and does not exceed 16; and provided that when o is zero then p is also zero.

17. The composition of claim 16, wherein not less than 80% by weight of the polyunsaturated fatty acids of the composition are comprised of the fatty acids represented by the formula when m is 4, n is 1, o is zero, p is zero and q is 7.

18. The composition of claim 16, wherein linoleic acid represents not less than 80% by weight of the polyunsaturated fatty acids of the composition.

19. The composition of claim 17, wherein the polyunsaturated fatty acid is present in the cis, cis configuration.

20. The composition of claim 18, wherein linoleic acid is present in the cis, cis configuration.

21. The composition of claim 16, wherein not less than 10% of the polyunsaturated fatty acids of the composition are comprised of the fatty acids represented by the formula when m is 1, n is 1, o is 1, p is 1, and q is 7.

22. The composition of claim 16, wherein linolenic acid represents not less than 10% of the polyunsaturated fatty acids of the composition.

23. The composition of claim 21, wherein the polyunsaturated fatty acid is present in the cis, cis, cis configuration.

24. The composition of claim 21, wherein linolenic acid is present in the cis, cis, cis configuration.

25. A method for reducing or eliminating shedding of hair by a human comprising: administering to the human, on a daily basis, a composition comprising safflower oil, sunflower oil, olive oil, soya oil, cod liver oil, lecithin, natural flavors, herbs, garlic, and zinc.

* * * * *